United States Patent [19]

Hirsbrunner et al.

[11] 4,075,329

[45] Feb. 21, 1978

[54] PROCESS FOR PROTECTING ORGANIC MATERIALS USING A BACTERIOSTATIC COFFEE EXTRACT

[75] Inventors: Pierre Hirsbrunner, Corseaux; Theodor Beyeler, Vevey; David Shepherd, Morges, all of Switzerland

[73] Assignee: Societe d'Assistance Technique pour Produits Nestle S.A., Lausanne, Switzerland

[21] Appl. No.: 679,321

[22] Filed: Apr. 22, 1976

Related U.S. Application Data

[63] Continuation of Ser. No. 556,290, March 7, 1975, abandoned.

[30] Foreign Application Priority Data

Apr. 8, 1974 Switzerland ............... 4907/74

[51] Int. Cl.$^2$ .................................................. A01N 9/08
[52] U.S. Cl. ......................................................... 424/195
[58] Field of Search ............................................ 424/195

[56] References Cited

PUBLICATIONS

Chemical Abstracts, vol. 78 (1973), p. 133523e.

*Primary Examiner*—V. D. Turner

[57] ABSTRACT

A process for protecting organic materials such as food-grade materials with a bacteriostatic agent, wherein an extract obtained from unroasted coffee is used as the bacteriostatic agent.

8 Claims, No Drawings

PROCESS FOR PROTECTING ORGANIC MATERIALS USING A BACTERIOSTATIC COFFEE EXTRACT

This is a continuation of application Ser. No. 556,290, filed Mar. 7, 1975, now abandoned.

This invention relates to a process for protecting organic materials, more especially food-grade materials, by means of a bacteriostatic agent extracted from unroasted coffee.

It is known that the growth of bacteria on or in organic materials can be retarded and even completely inhibited by the addition of a bacteriostatic agent. There are a large number of active substances which are suitable for this purpose, including for example phenyl mercuric borate, hexachlorophene, sulphur dioxide, benzoates. Unfortunately, problems are involved in the use of substances of this kind in the food industry (toxicology, laws, etc.). It is for this reason that the food industry has turned towards natural substances or extracts. Various bacteriostatic agents have been prepared from plants, above all from spices, for example from celery oil, caraway oil, clove oil, etc. Unfortunately, spices being by definition materials with distinctive flavours and odours, it is almost impossible to prepare by extraction bacteriostatic agents completely free of any organoleptic component. In addition, these agents are not very active or, more precisely, if they are very active, their activity is highly specific and they have to be used in considerable quantities. As a result, they impart their flavour and odour to the food-grade products to which they are added.

The present invention relates to a process for protecting organic materials, especially food-grade materials, by means of a bacteriostatic agent of remarkable activity which, organoleptically, does not betray its origins. The process according to the invention is distinguished by the fact that an extract obtained from unroasted coffee is used as the bacteriostatic agent.

This bacteriostatic agent is obtained by treating coffee waxes, that is to say the film of fat surrounding the grain of unroasted coffee. The waxes themselves do not have any significant bacteriostatic effect because the bacteriostatic agent present in them is too diluted. It is for this reason that the bacteriostatic agent is isolated by the treatment referred to above which comprises at least one so-called acid-base extraction of the type normally applied in the field of chemistry, for example a distribution between a solvent phase and a basic aqueous phase, followed after decantation and separation by acidification of the basic aqueous phase and then by distribution between a solvent phase and the aqueous phase thus acidified, separation of the solvent phase and evaporation of the solvent in cases where it is desired to recover the bacteriostatic agent in dry form. In one advantageous method of extraction, the caffeine present in the unroasted coffee is simultaneously extracted by any known decaffeination process using a solvent, after which the caffeine extraction residue is treated by a process comprising various purifications to eliminate the caffeine, and an acid-base extraction such as, for example, the acid-base extraction defined above.

The residue obtained in this way represents the bacteriostatic agent. It has an oily consistency, is yellowish to brownish in colour, has a moderate inherent taste and odor and is perfectly edible. It shows remarkable bacteriostatic activity which is governed to some extent by the method of extraction used and, in particular, by the type of solvent(s) used. It is possible to use a wide variety of water immiscible solvents, such as methylene chloride, hexane, ethyl acetate, although the best effects are achieved with agents obtained by extraction with diethyl and diisopropyl ethers.

The results of preliminary chromatographic tests show that this bacteriostatic agent is in the form of a complex mixture of several substances of unknown type. In addition, it would seem that most of the bacteriostatic power derives from one or two substances and not from all the constituent substances of this mixture. Owing to its method of preparation, the whole has an acid character, but is non-phenolic in nature, as shown by the negative results of ferric chloride tests, so that the substances in question are not tannins. Providing it is not stored in dry form, the agent is stable at temperatures of up to approximately 60° C and keeps well in air.

The bacteriostatic agent may be added to finished organic materials, more especially to food-grade materials ready for consumption, in quantities by weight of at least 0.15%, i.e., 1.5 mg of dry agent per g of dry materials. In the case of a processed material, addition of the agent may thus form the last stage in the manufacturing process or may be made at any stage during manufacture, so that the agent is unable to undergo any changes as a result. It may be added for example in solution or emulsion in a suitable carrier or solvent. The quantities normally used are slightly greater than the minimum dose by which bacterial growth is inhibited, for example 2 times greater, and have to be adapted according to the particular type of material to be protected and to the environmental conditions, especially the climatic conditions. In addition, the bacteriostatic agent may be used as a bactericide, the doses required in that case being approximately 3 times greater. When used in doses of this order, the bacteriostatic agent, which has only a slight odour and flavour, is too dilute to impart its odour and flavour to the food-grade material.

This agent may of course be added in admixture with other substances, such as antioxidants, flavourings, colorants, etc. Finally, where practical requirements dictate, it is possible to treat only part of the organic material with the bacteriostatic agent in one form or another and then to mix the material thus treated with the rest of the untreated material. It is then advisable to subject the mixture to careful homogenisation.

In one preferred embodiment of the process according to the invention, the bacteriostatic agent is added in such a way that its concentration in the end food product is in the range from 0.15 to 0.6%, i.e., in the range from 1.5 to 6 mg of dry agent per g of dry matter.

In a first modification of this embodiment, the bacteriostatic agent is prepared by directly treating unroasted coffee with methylene chloride in a quantity of approximately 10 parts by weight of methylene chloride to 1 part by weight of unroasted coffee. Evaporation of the methylene chloride leaves a greasy residue which is taken up in an aqueous alkaline soda solution with a pH-value of from 10 to 12. After vigorous stirring at a temperature in the range from 20° to 30° C, the product is decanted and the supernatant fat phase is separated off. The aqueous phase is then acidified with a 1 N to 5 N sulphuric acid solution until a pH-value in the range from 1 to 2 is obtained. This acidified aqueous phase is then extracted with diethyl ether or diisopropyl ether, for example with 3 times the same volume of diisopropyl ether, after which the bacteriostatic agent is recovered by evaporating the ether, optionally after drying with an anhydrous salt. It is preferred to keep the agent in solution, even in concentrated solution, rather than in dry form. In this case, the ether does not have to be evaporated to dryness, or the bacteriostatic agent is redissolved, for example in alcohol. It is also possible before evaporation to change the solvent, for example by adding alcohol to the ethereal phase, removing the ether and optionally concentrating the alcoholic phase containing the bacteriostatic agent.

In a second modification of this embodiment, the decaffeination residues obtained for example by treating previously moistened unroasted coffee with methylene chloride are used as starting material. It is known that the water thus applied to the coffee beans makes them swell and, at the same time, causes the caffeine/chlorogenic acid complex to dissociate. Accordingly, the caffeine accompanies the waxes into the methylene chloride, so that evaporation of the methylene chloride leaves a fatty residue rich both in crystallised caffeine and in water. It is then possible as required either to filter the undissolved caffeine, to separate the waxes from the aqueous phase and then to treat the waxes thus separated with an alkaline solution, or to take up the residue in an acid solution of pH 1 - 2, to separate the waxes from the aqueous acid phase, in which the caffeine is dissolved, and then to treat the waxes with an alkaline solution, or even to combine the purification processes described above. In both cases, the treatment by which the bacteriostatic agent is isolated is with advantage continued in the same way as described earlier on in reference to the first embodiment. These operations involving crystallisation or dissolution in acid medium may of course be repeated as many times as necessary in order suitably to remove the caffeine before the alkaline treatment of the waxes.

The process according to the invention is illustrated by the following Examples. Examples 1 and 2 relate to the extraction of the bacteriostatic agent, Example 3 describes the tests demonstrating the bacteriostatic power of the agent, while Example 4 demonstrates the effectiveness of the bacteriostatic agent in protecting food-grade materials against microbial growth.

EXAMPLE 1

240 kg of unroasted coffee beans are treated with vigorous stirring at 20° C with 3 separate 800 liter batches of methylene chloride. These 3 volumes of liquid phase are combined and the methylene chloride removed in vacuo, leaving 2.5 kg of a greasy residue greenish in color with an odor of unroasted coffee which is immediately treated with 10 liters, and then 8 liters and then another 8 liters of a 0.05 N aqueous soda solution at a temperature of 25° C. After each operation, the mixture is left to settle, after which the supernatant fatty phase is separated from the aqueous phase. These 3 volumes of aqueous alkaline phase are then combined and then acidified to pH 1 with 0.3 liter of a 5 N sulphuric acid solution. This aqueous acidified phase is then extracted with 3 volumes of diethyl ether measuring 25 liters, 20 liters and 20 liters, respectively, after which the 3 volumes of ethereal phase are combined. 10 liters of ethanol are then added to the ethereal phase, after which the ether is removed in vacuo at a temperature kept below 30° C. Finally, most of the ethanol is evaporated in vacuo at a temperature of approximately 35° C, leaving approximately 1 liter of an alcoholic solution containing 18 g of bacteriostatic agent which is maintained in this form.

EXAMPLE 2

60 kg of water are added to 240 kg of unroasted coffee beans at a temperature of 60° C and under a pressure of 1.5 atms. After a contact time of 1 hour, the pressure is reduced to 1 atm and the swollen beans are treated with 6 times 320 liters of methylene chloride. These 6 volumes of liquid phase are combined, after which the methylene chloride is removed in vacuo, leaving 10.2 kg of a non-homogeneous brown-green mixture, with the odour of unroasted coffee, consisting of a fatty phase and an aqueous phase containing crystals of caffeine. The caffeine is removed by filtration (2.5 kg). The two liquid phases are then separated, followed by the successive addition to the fatty phase of three separate 12.5 liter batches of a 0.05 N sulphuric acid solution. After each operation, the mixture is left to settle, the two phases are separated and the fatty phase recovered. On completion of these purifying operations, the fatty phase no longer contains caffeine. It is then treated with 10 liters of a 0.05 N aqueous soda solution, and separation of the bacteriostatic agent is continued in the same way as described in Example 1, except that diisopropyl ether is used as the extraction solvent. The proportions of solvent used are the same or equivalent. 1 liter of an alcoholic solution containing 20 g of bacteriostatic agent is thus obtained, the bacteriostatic agent being maintained in that form.

EXAMPLE 3

The bacteriostatic activity of the agent was assessed by the minimum inhibition concentration method of the Public Health Laboratory Service Committee described in British Med. J. 408 (1965).

Five cultures of the following microorganisms are prepared:

bacteria:*Escherichia coli* ATCC 8739, *Staphylococcus aureus* ATCC 155, *Pseudomonas aeruginosa* ATCC 10145, *Bacillus cereus* ATCC 14579.

yeast:*Candida utilis* CBS 567.

containing approximately $2.10^8$ cells/ml of nutrient medium (culture time approximately 24 hours).

At the same time, samples of the bacteriostatic agent to be tested are prepared by dilution from a mother suspension (2 g/100 ml, i.e., 2/100) in ethanol. 1 ml of water is added to a first 1 ml sample of this mother suspension, 2 ml of water are added to a second sample, and so on, so as to obtain a series ranging in dilution from 1/100 to 1/300, after which this intermediate series and the initial mother suspension are diluted 10 times with the nutrient medium of microorganisms. A series of test samples ranging in dilution from 1/500 to 1/3000 is prepared in this way.

0.2 ml of each of the aforementioned microorganism cultures are then added to 10 ml of each of the diluted samples thus prepared. This is followed by incubation for 24 hours at 30° C for the bacteria and at 35° C for the yeast, after which the optical density of the mixture is measured at 600 nm and compared with the optical density of reference samples.

Here now are the minimum inhibition concentrations found for the "diisopropylic" agent prepared in Example 2:

1/2500 against *Ps. aeruginosa*
1/1000 against *E. coli, Staph. aureus, B. cereus*
no bacteriostatic activity against *C. utilis*

The minimum inhibition concentrations for the "diethylic" agent prepared in Example 1 are approximately 2 times higher.

EXAMPLE 4

4 groups of 4 sterile samples of reconstituted skimmed milk, i.e., a total of 16 samples, are prepared and then inoculated with the bacteria mentioned in Example 3 and protected against them by variable doses of the bacteriostatic agent prepared in Example 2. Evolution of the colonies of bacteria in the samples incubated at 30° C is then measured as a function of time by a conventional counting method. The results are set out in the following Table:

| incubation time in h | % of bacteriostatic agent added | number of bacteria present per ml of skimmed milk | | | |
|---|---|---|---|---|---|
| | | Staph. aureus | E. coli | B. cereus | Ps. aeruginosa |
| 0 (inoculation) | 0 (control) | 210 | 860 | 60 | 220 |
| | 0.5 | 160 | 740 | 60 | 170 |
| | 1 | 210 | 870 | 50 | 190 |
| | 2 | 170 | 850 | 40 | 230 |
| 4 | 0 (control) | 3800 | 3000 | 3000 | 9200 |
| | 0.5 | 1600 | 18000 | 2300 | 1600 |
| | 1 | 800 | 1000 | 60 | 500 |
| | 2 | 100 | 20 | 30 | 75 |
| 8 | 0 (control) | 650000000 | 870000000 | 12000000 | 290000000 |
| | 0.5 | 520000 | 300000 | 300000 | 340000 |
| | 1 | 8000 | 110000 | 350 | 47000 |
| | 2 | 200 | 10 | 20 | 1500 |
| 24 | 0 (control) | 230000000 | *780000000 | *12000000 | 175000000 |
| | 0.5 | 140000000 | 460000000 | 5800000 | 300000000 |
| | 1 | 100000000 | 300000000 | 6500000 | 140000000 |
| | 2 | 150 | 10 | 10 | 120000000 |

*coagulated samples

In the above Table, the percentages of bacteriostatic agent added are percent of a 3% ethanolic solution of that agent in skimmed milk which itself has a solids content of approximately 10%. Accordingly, these percentages express the following quantities by weight:

0.5% = 0.5 ml/100 ml = 1.5 mg/g of solids
1% = 1 ml/100 ml = 3 mg/g of solids
2% = 2 ml/100 ml = 6 mg/g of solids Naturally the figures quoted in the above Table are by no means precise and are to be considered above all as orders of magnitude. Nevertheless it can be seen that the bacteriostatic agent is extremely effective in inhibiting bacterial growth, except perhaps in the long term with respect to *Ps. aeruginosa*, for this particular substrate of skimmed milk.

We claim:

1. A process of obtaining a bacteriostatic agent from unroasted coffee beans comprising the steps of
    contacting a mass of unroasted coffee beans with an organic solvent phase and a basic aqueous phase,
    thereafter decanting and separating the basic aqueous phase,
    acidifying the separated basic phase,
    thereafter contacting the acidified aqueous phase with an organic solvent phase, and
    then separating the solvent phase containing the bacteriostatic agent.

2. A process of obtaining a bacteriostatic agent from unroasted coffee beans comprising the steps of
    subjecting a mass of unroasted coffee beans to a decaffeination process using a solvent to obtain a caffeine extraction residue;
    purifying the residue to eliminate caffeine;
    thereafter subjecting the caffeine-free residue to an acid-base extraction by contacting the residue with a solvent phase and a basic aqueous phase,
    thereafter decanting and separating the basic aqueous phase,
    acidifying the separated basic aqueous phase,
    thereafter contacting the acidified aqueous phase with an organic solvent phase, and
    then separating the solvent phase containing the bacteriostatic agent.

3. A process of obtaining a bacteriostatic agent comprising the steps of
    treating unroasted coffee beans with an organic solvent;
    thereafter evaporating the organic solvent to obtain a greasy residue;
    placing the residue into an aqueous solution with a pH-value of from 10 to 12;
    stirring the residue-containing solution;
    thereafter decanting the solution and separating off the supernatant fat phase;
    then acidifying the aqueous phase of the decanted solution until a pH-value in the range of from 1 to 2 is obtained; and
    extracting the acidified aqueous phase with an organic solvent, said acidified aqueous phase containing the bacteriostatic agent.

4. A process of obtaining a bacteriostatic agent comprising the steps of
    treating previously moistened unroasted coffee beans with methylene chloride to obtain decaffeination residues;
    thereafter evaporating the methylene chloride from the residues to obtain a fatty residue rich in crystallized caffeine and water;
    filtering out the undissolved caffeine;
    separating the resulting residue from the aqueous phase;
    placing the residue into an aqueous alkaline soda solution with a pH-value of from 10 to 12;

stirring the residue-containing solution at a temperature in the range of 20° to 30° C;

thereafter decanting the solution and separating off the supernatant fat phase;

then acidifying the aqueous phase of the decanted solution with a 1N to 5N sulphuric acid solution until a pH-value in the range of from 1 to 2 is obtained; and extracting the acidified aqueous phase with one of diethyl ether or dissopropyl ether, said acidified aqueous phase containing the bacteriostatic agent.

5. A process of obtaining a bacteriostatic agent comprising the steps of treating previously moistened unroasted coffee beans with methylene chloride to obtain decaffeination residues;

thereafter evaporating the methylene chloride from the residues to obtain a fatty residue rich in crystallized caffeine and water;

taking up the residue in an acid solution of pH 1 to 2;

separating the residue from the aqueous acid phase in which the caffeine is dissolved;

placing the residue into an aqueous alkaline soda solution with a pH-value of from 10 to 12;

stirring the residue-containing solution at a temperature in the range of 20° to 30° C;

thereafter decanting the solution and separating off the supernatant fat phase;

then acidifying the aqueous phase of the decanted solution with a 1N to 5N sulphuric acid solution until a pH-value in the range of from 1 to 2 is obtained; and extracting the acidified aqueous phase with one of diethyl ether or dissopropyl ether, said acidified aqueous phase containing the bacteriostatic agent.

6. A process of obtaining a bacteriostatic agent comprising treating unroasted coffee beans with vigorous stirring at 20° C with separate batches of methylene chloride;

combining the batches of methylene chloride and removing the methylene chloride to obtain a greasy residue;

treating the residue with a batch of 0.05N aqueous soda solution at a temperature of 25° C;

thereafter allowing the residue-containing solution to settle and then separating the supernatant fatty phase from the aqueous phase;

repeating said steps of treating the residue with the aqueous soda solution and separating the fatty phase from the aqueous phase;

acidifying the aqueous phase to a pH of 1 with a 5N sulphuric acid solution;

extracting the acidified phase with successive volumes of diethyl ether and combining the ethereal phases;

adding ethanol to the ethereal phases and thereafter removing ether; and evaporating the ethanol leaving an alcoholic solution containing the bacteriostatic agent.

7. A process of obtaining a bacteriostatic agent comprising the steps of adding water to unroasted coffee beans at a temperature of 60° C and a pressure of 1.5 atmospheres;

reducing the pressure to 1 atmosphere after 1 hour;

thereafter treating the beans with methylene chloride to obtain a liquid phase;

removing the methylene chloride from the liquid phase to obtain a mixture consisting of a fatty phase and an aqueous phase containing crystals of caffeine;

filtrating the mixture to remove the caffeine;

thereafter separating the two liquid phases and adding a sulphuric acid solution to the fatty phase;

allowing the mixture to settle and thereafter again separating the two phases to recover the fatty phase;

adding an aqueous soda solution to the fatty phase;

acidifying the aqueous phase to a pH of 1 with a 5N sulphuric acid solution;

extracting the acidified phase with successive volumes of dissopropyl ether and combining the ethereal phases;

adding ethanol to the ethereal phases and thereafter removing ether; and evaporating the ethanol leaving an alcoholic solution containing the bacteriostatic agent.

8. A process for protecting foodstuffs comprising adding thereto a bacteriostatic agent in a quantity of at least 1.5 mg/g of dry matter, said bacteriostatic agent being obtained by contacting a mass of unroasted coffee beans with an organic solvent phase and a basic aqueous phase, thereafter decanting and separating the basic aqueous phase, acidifying the separated basic aqueous phase, thereafter contacting the acidified aqueous phase with an organic solvent phase, and then separating the solvent phase containing the bacteriostatic agent.

* * * * *

UNITED STATES PATENT AND TRADEMARK OFFICE
CERTIFICATE OF CORRECTION

PATENT NO. : 4,075,329
DATED : February 21, 1978
INVENTOR(S) : Pierre Hirsbrunner, Theodor Beyeler, Shepherd Morges It is certified that error appears in the above-identified patent and that said Letters Patent are hereby corrected as shown below:

Column 7, line 11, change "dissopropyl" to -- diisopropyl --

Column 7, line 38, change "dissopropyl" to -- diisopropyl -- column 8, line 34, change "dissopropyl" to -- diisopropyl --

Signed and Sealed this

Sixth Day of June 1978

[SEAL]

Attest:

RUTH C. MASON
Attesting Officer

DONALD W. BANNER
Commissioner of Patents and Trademarks